US005769884A

United States Patent [19]

Solovay

[11] Patent Number: 5,769,884
[45] Date of Patent: Jun. 23, 1998

[54] CONTROLLED POROSITY ENDOVASCULAR IMPLANT

[75] Inventor: Kenneth S. Solovay, Fort Lauderdale, Fla.

[73] Assignee: Cordis Corporation, Miami Lakes, Fla.

[21] Appl. No.: 671,387

[22] Filed: Jun. 27, 1996

[51] Int. Cl.$^6$ ..................................................... A61F 2/06
[52] U.S. Cl. .................................. 623/1; 623/12; 606/194
[58] Field of Search .................. 623/1, 16; 606/190–200

[56] References Cited

U.S. PATENT DOCUMENTS

| | | |
|---|---|---|
| 4,255,820 | 3/1981 | Rothermel et al. ............................. 3/1 |
| 4,321,711 | 3/1982 | Mano ........................................... 3/1.4 |
| 4,733,665 | 3/1988 | Palmaz . | 
| 4,743,252 | 5/1988 | Martin, Jr. et al. .......................... 623/1 |
| 4,816,339 | 3/1989 | Tu et al. .................................. 428/421 |
| 4,878,906 | 11/1989 | Lindemann et al. . |
| 4,921,495 | 5/1990 | Kira ........................................... 623/1 |
| 5,019,090 | 5/1991 | Pinchuk . |
| 5,024,669 | 6/1991 | Peterson et al. ........................... 623/13 |
| 5,024,671 | 6/1991 | Tu et al. ..................................... 623/1 |
| 5,084,065 | 1/1992 | Weldon et al. .............................. 623/1 |
| 5,104,399 | 4/1992 | Lazarus ....................................... 623/1 |
| 5,123,917 | 6/1992 | Lee . |
| 5,135,536 | 8/1992 | Millstead . |
| 5,152,782 | 10/1992 | Kowligi et al. ............................. 623/1 |
| 5,282,824 | 2/1994 | Gianturco . |
| 5,330,500 | 7/1994 | Song . |
| 5,413,598 | 5/1995 | Moreland ................................... 623/1 |

FOREIGN PATENT DOCUMENTS 277678   8/1988   European Pat. Off. ....................... 2/2

OTHER PUBLICATIONS

"Biocompatibilty of Clinical Implant Materials, vol. II", M. King et al., pp. 177–207, CRC Press, Inc.

"Relation of pore size to tissue ingrowth in prosthetic heart valves: An experimental study", Surgery, N.S. Braunwald et al., May 1965, pp. 741–747.

"Transluminally–placed Coilspring Endarterial Tube Grafts", Investigative Radiology, C.T. Dotter, 9:329–332, 1969.

"Tissue Ingrowth and Porosity of Biomer", Trans Am Soc Artif Org, E. Pollack et al., vol. XXVII, pp. 405–409, 1981.

"An Experimental Study of the Influence of Pore Size of Implanted Polyurethane Sponges upon Subsequent Tissue Formation", Surgery, Gynecology & Obstetrics, J.E. salvatore et al. Apr. 1961, pp. 463–468.

"Porosity: primary determinant of ultimate fate of synthetic vascular grafts", Surgery, S.A. Wesolowski et al., Jul. 1961, pp. 91–96.

*Primary Examiner*—David Isabella
*Assistant Examiner*—John M. Black
*Attorney, Agent, or Firm*—Watts, Hoffmann, Fisher & Heinke Co., LPA

[57] ABSTRACT

A covered stent for treating a stenotic region in a blood vessel. The stent covering has different porosities in different regions. In those regions, typically the ends, where tissue ingrowth and re-endothelialization are desired, the stent covering is more porous, and in those regions were it is desirable to inhibit such ingrowth, the stent covering is substantially non-porous.

23 Claims, 3 Drawing Sheets

CONTROLLED POROSITY ENDOVASCULAR IMPLANT

BACKGROUND OF THE INVENTION

The present invention relates generally to a controlled porosity endoprosthesis implant and, more specifically, to a stent covering for treating a damaged or stenotic artery or blood vessel.

Endoprosthesis implants, and more particularly stents, are commonly used to treat restenosis of blood vessels or other damaged passageways or ducts in the body, like bronchi or the esophagus. These devices are often used as adjuncts to balloon angioplasty to reduce the amount of artery recoil, blockage return or restenosis after the angioplasty procedure has been performed. Different designs of stents include balloon expanded, self-expanded and/or thermally expanded designs that do not use a balloon for initial delivery. A stent is implanted into a stenotic region of a damaged vessel such that its length bridges the damaged portion and its ends engage undamaged or healthy tissue. The stent re-expands the opening of the vessel thus allowing improved blood flow.

Covered stents, and vascular grafts sutured to stents, may be used to treat restenosis of atherosclerotic disease and clot-filled arteries that are not successfully treated with angioplasty or bare stents. Because these arteries often require invasive surgical by-pass grafting which may jeopardize a patient's survival, a covered stent is a desirable alternative. Other vascular diseases can also be treated with covered stents, including aneurysms, arterio-venous (A-V) fistulas, trauma, dissections, shunts through the liver, and malignant stenosis of biliary ducts.

Covered stent implants may be comprised of a stent having an expandable frame structure covered with a polymer material such as polytetrafluoroethylene (PTFE). If the material is porous then cells, tissue and capillaries can penetrate through the pores, thereby preventing migration of the endoprosthesis implant and allowing the blood vessel to be re-endothelialized with new healthy tissue. However, if the stent covering is too porous, there may be a tendency for diseased tissue to transfer itself to the newly created intima and damage the healthy tissue. Conversely, if the stent covering or vascular graft is non-porous, or substantially non-porous, it can seal-off blood flow from defects in the wall of a vessel, prevent clot or tissue from protruding into a vessel lumen, and provide a smoother lumen for better blood flow. However, this may also unduly inhibit or restrict desired healthy tissue ingrowth and re-endothelialization. Vascular grafts typically only allow approximately 1 cm of endothelial ingrowth from a sutural anastomosis site. Thus, any nonporous covered stent longer than about 2 cm cannot re-endothelialize and, as a consequence, increases the likelihood of restenosis.

Thus, the porosity of the stent covering, or vascular graft, presents a tradeoff problem; a porous covering may permit healthy tissue ingrowth but may also have a detrimental effect of allowing unwanted damaged tissue ingrowth; and, anonporous covering may inhibit damaged tissue ingrowth, but will also inhibit desired healthy tissue ingrowth.

DISCLOSURE OF THE INVENTION

The present invention provides a controlled porosity endoprosthesis implant, or covered stent, for use in treating a damaged or stenosed blood vessel, reducing hyperplasia and the like, and promoting and controlling endovascular ingrowth.

In one aspect of the present invention, the endoprosthesis implant includes a stent having an expandable frame structure as is known in the art, and a polymeric stent covering. The porosity of the stent covering varies along different portions thereof. The regions of the stent covering near the ends of the stent preferably have pores to allow healthy tissue ingrowth and re-endothelialization. The middle portion of the stent covering preferably is substantially less porous than the end portions of the stent covering, or non-porous, in order to encapsulate the damaged or diseased tissue.

When deployed, the ends of the stent bridge the damaged or diseased portion of the blood vessel and have an outside diameter slightly larger than the inside diameter of the blood vessel. The porous portions of the stent covering promote healthy tissue and capillary ingrowth near the ends of the stent, which helps keep the stent from migrating, and promotes re-endothelialization along the entire length of the endoprosthesis implant. The less porous or non-porous portion of the stent covering helps prevent the diseased segment of the vessel from travelling to the newly formed intima by encapsulating it between the vessel wall and the stent.

According to another feature of the invention, the porosity of the stent covering may be especially fabricated from fibers or a continuous polymeric sheet. The fibers may be knitted, woven or braided to achieve one desired porosity near the end regions and a different porosity in the middle portion of the stent covering. Alternatively, different porosities may be achieved by using a polymeric material in which pores are formed by techniques such as laser drilling or by dissolving portions of the covering by chemical action.

Thus, in one aspect of the invention there is provided an endoprosthesis implant comprising a stent having an expandable frame structure and a stent covering disposed on the stent. Tie stent covering includes first and second regions each having a plurality of pores which define a first and second porosity, respectively. The pores in the first region have a diameter of about 30 to about 120 micrometers. The second region, which has fewer pores or smaller pores than the first region, or no pores, is substantially impermeable to the passage of tissue ingrowth. The impermeability substantially inhibits diseased tissue from penetrating the endoprosthesis stent covering and possibly contaminating the surrounding healthy tissue.

According to the invention, the stent covering comprises a plurality of woven, braided, or knitted fibers. In the preferred embodiment, the fibers have an average diameter that is larger than the average pore diameter of the pores in the first region. Also, the average diameter of the fibers is preferably at least about three times the pore diameter of the pores in the first region. In another preferred embodiment, the average diameter of the fibers is at least three times the shortest pore width. This substantially prevents phagocytic cells from triggering an inflammatory response.

According to another feature of the invention, the stent covering comprises a continuous polymeric sheet having pores interspersed in the first region. The pores are spaced apart a distance of at least three times the average pore diameter of the pores in the first region. In this embodiment, the second region is substantially impermeable to body fluids. In another preferred embodiment, the pores are spaced apart a distance of at least three times the shortest pore width.

These and other features of the invention will be better understood from a detailed description of alternate embodiments of the invention which are described in conjunction with the accompanying drawings.

DETAILED DESCRIPTION OF THE PREFERRED EMBODIMENTS

Figure 1:
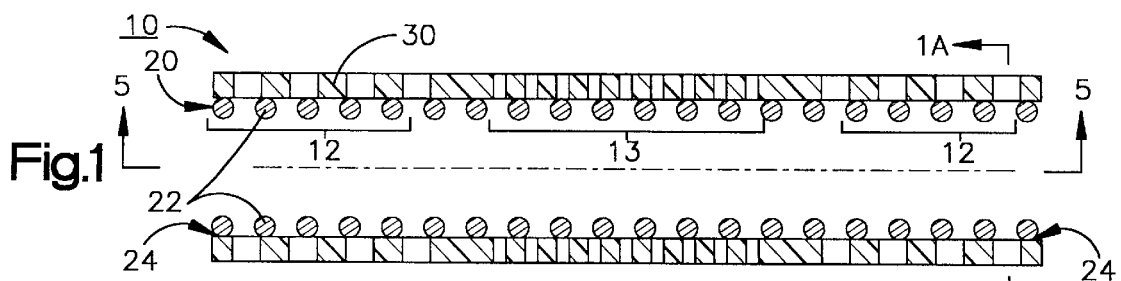
FIG. 1 is a schematic depiction of a nonuniform porosity endoprosthesis implant in accordance with the present invention when the stent covering is woven or braided.
Figure 1A:
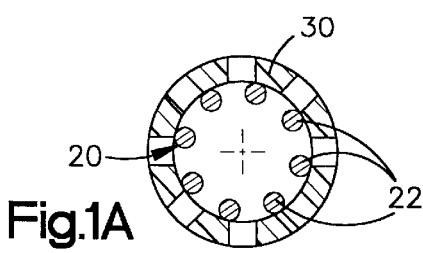
FIG. 1A is a cross section view of the endoprosthesis implant in FIG.1 as seen from the plane 1A—1A in FIG.1.
Figure 2:
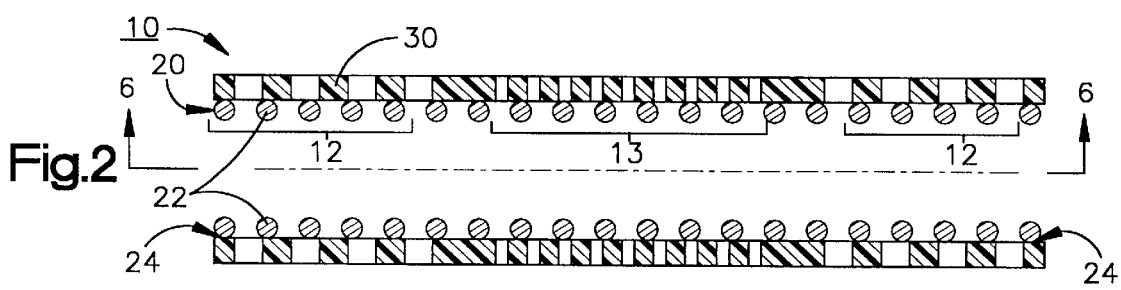
FIG. 2 is a schematic depiction of a nonuniform porosity endoprosthesis implant in accordance with the present invention when the stent covering comprises a laser drilled or chemically treated polymeric sheet.

FIG. 1 illustrates the overall construction of an endoprosthesis implant 10 in accordance with a preferred embodiment of the invention. The endoprosthesis implant 10 includes a stent 20 having an expandable frame structure 22 and a stent covering 30 with regions 12, 13 having different porosities. The stent covering 30 can be fabricated directly onto the stent 20 by, for example, weaving or braiding the material directly onto the expandable frame structure 22, or by disposing a polymeric sheet onto the frame structure 22 (as shown in FIG. 2).

Figure 3:
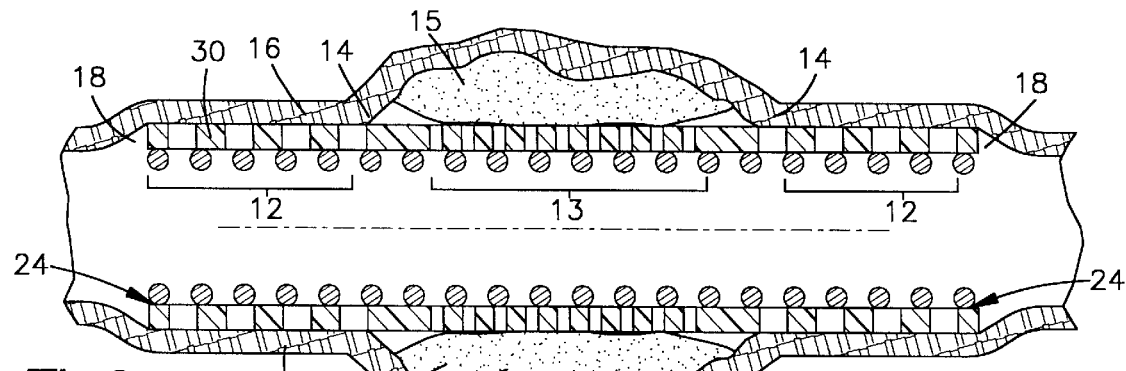
FIG. 3 is a schematic depiction of a nonuniform porosity endoprosthesis implant in accordance with the present invention implanted in a blood vessel.

Referring to FIG. 3, the stent 20 is comprised of ends 24 spaced apart a distance greater than the length of the damaged region 15 of the blood vessel 16. When in its expanded state, the outer diameter of the stent 20 and the expandable frame structure 22 is greater than the inner diameter of the blood vessel 16, effectively causing an interference fit 18 between the implant 10 and the blood vessel 16 thereby inhibiting migration of the endoprosthesis implant 10.

As FIG. 3 illustrates, the endoprosthesis implant 10 is placed in the blood vessel 16 so its end portions 12 engage healthy tissue 14 and bridge damaged or diseased tissue 15 of the blood vessel 16. The middle portion 13 of the endoprosthesis implant 10 is interposed between the end portions 12 and covers the damaged tissue 15.

Figure 4:
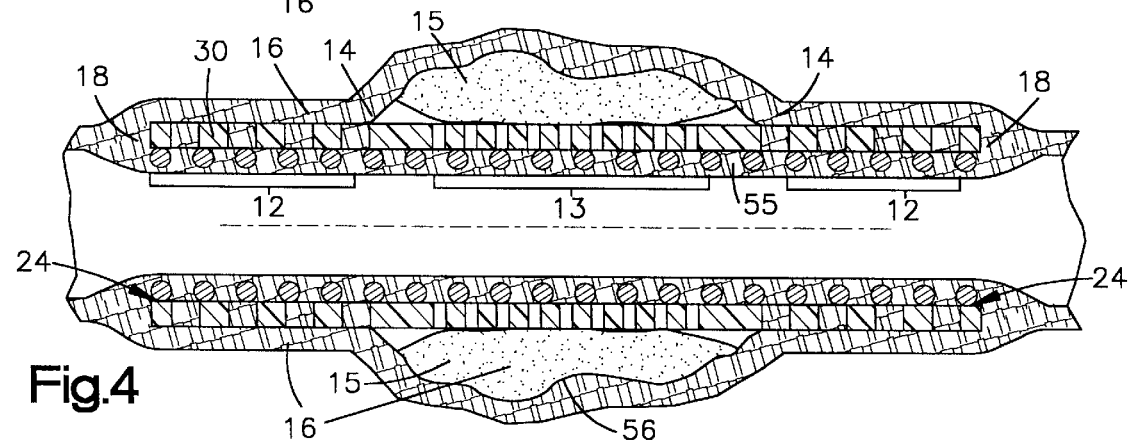
FIG. 4 is a schematic depiction of a nonuniform porosity endoprosthesis implant in accordance with the present invention implanted in a blood vessel conceptually showing healthy tissue ingrowth.
Figure 5:
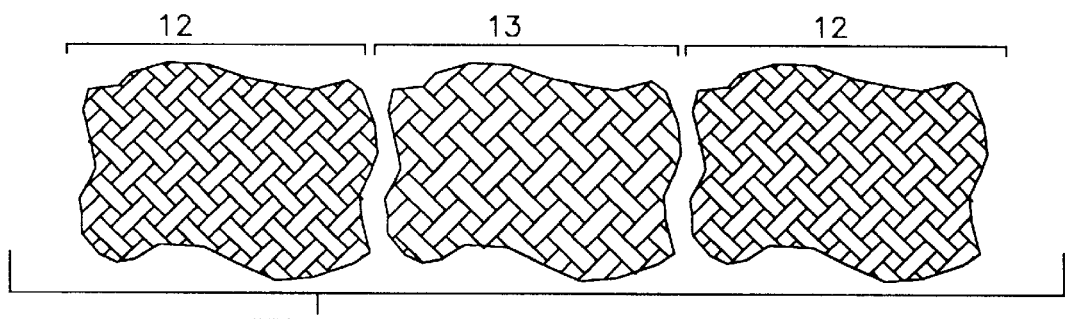
FIG. 5 is a cross section view as seen from the plane 5—5 in FIG.1, conceptually showing the different porosities of the endoprosthesis implant when the stent covering is woven or braided.
Figure 6:
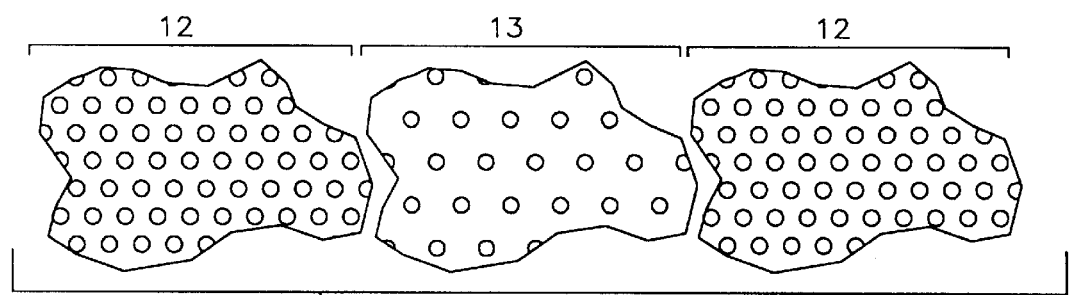
FIG. 6 is a cross section view as seen from the plane 6—6 in FIG.2, conceptually showing the different porosities of the endoprosthesis implant when the stent covering comprises a laser drilled or chemically treated polymeric sheet.
Figure 5A:
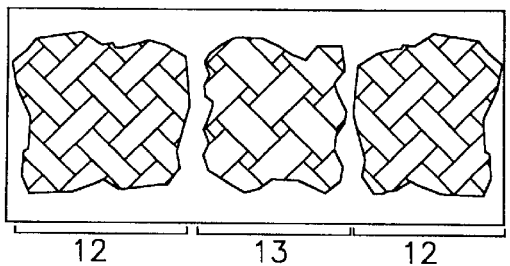
FIGS. 5A to 5E are cross section views as seen from the plane 5—5 in FIG. 1, conceptually showing alternative different porosities of the endoprosthesis implant when the stent covering is woven or braided.
Figure 6A:
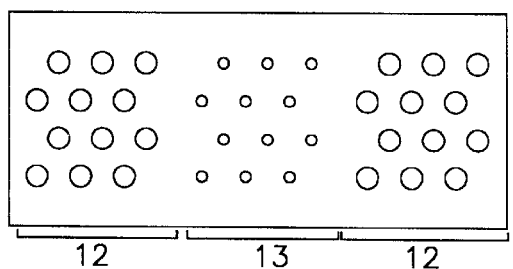
FIGS. 6A to 6E are cross section views as seen from the plane 6—6 in FIG.2, conceptually showing alternative different porosities of the endoprosthesis implant when the stent covering comprises a laser drilled or chemically treated polymeric sheet.
Figure 5B:
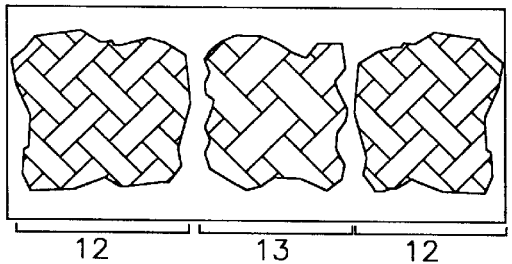
Figure 6B:
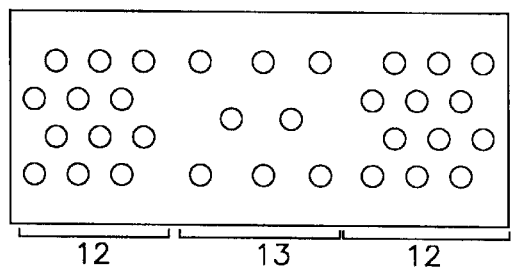
Figure 5C:
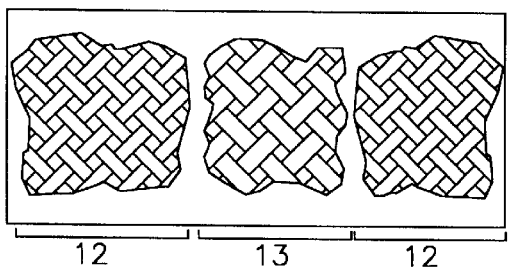
Figure 6C:
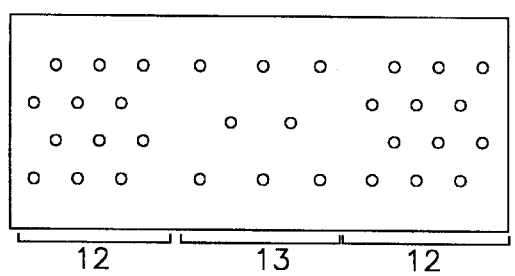
Figure 5D:
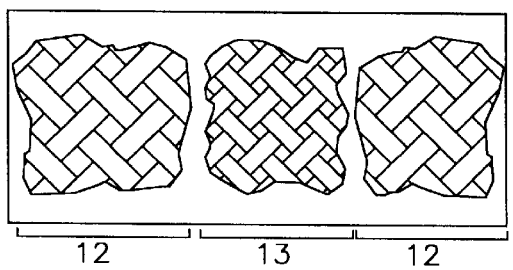
Figure 6D:
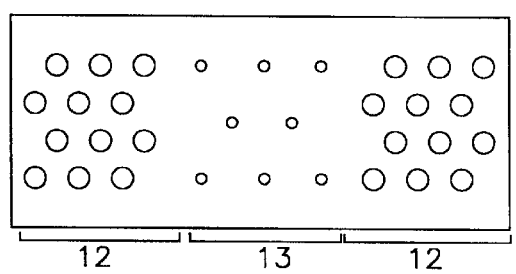
Figure 5E:
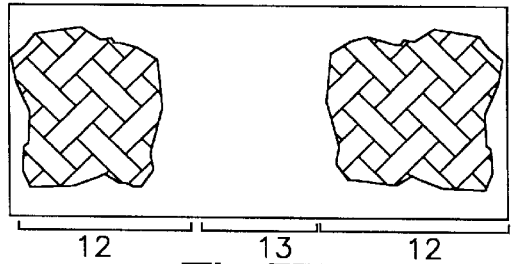
Figure 6E:
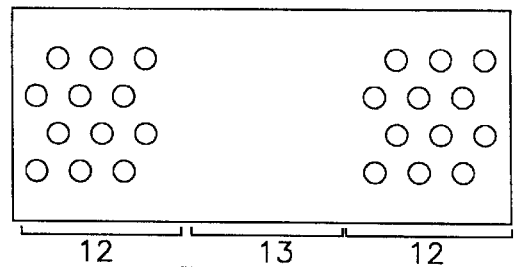

As seen in FIGS. 1 through 4, the end portions 12 and the middle portion 13 of the stent covering 30 have different porosities. Different porosity may be characterized by a difference in pore size, a difference in pore density or both. FIGS. 5 and 6 are illustrative of how the porosity may differ in accordance with the present invention. A particular region 13 may be less porous than another region 12 because it has smaller pores (as conceptually shown in FIGS. 5a and 6a), fewer pores (as conceptually shown in FIGS. 5b, 5c, 6b, and 6c), both smaller and fewer pores (as conceptually shown in FIGS. 5d and 6d), or no pores (as conceptually shown in FIGS. 5e and 6e).

As used herein, the term "pore" refers to a void or opening in the stent covering material 30. A pore may comprise a direct passage through the stent covering 30 from the outer surface to the inner surface, or a pore may comprise a passage or passages from an opening or void in the outer surface of the stent covering 30 to the inner surface through a plurality of interconnected passages through the volume of the stent covering material 30. In some instances, the pores may not even pass all the way through the covering 30. The shape of a pore can vary dramatically depending on the nature of stent covering 30 and how it, or the pore, is formed. What is important is that, in the desired portions of the covering 30, the pores provide a lattice for tissue ingrowth allowing cells and blood vessels to travel and grow into and/or through the stent covering 30. As such, it is the porosity of the as-deployed stent covering 30 that is important since it is the as deployed pore spacing and dimensions that control the type and rate of cellular ingrowth.

In the case of the present invention, the most important pore parameters are pore diameter which, as used herein refers to the average diameter of a pore or opening at the outer surface of the covering 30, pore spacing, which is the average distance between pores or openings on the surface of the covering 30, and the smallest pore width, which is the smallest dimension of a given opening at the surface of the cover 30. Pore diameter is important when relating the relative size of pores in one portion of the covering 30 as compared to the relative size of pores in another portion. For example, on average, the pore diameter of the pores in portion 12 can be characterized as being larger than the pore diameter of the pores in portion 13. Thus, when characterizing such a stent, one can say that the average pore diameter in portion 12 is larger than the average pore diameter in portion 13. Pore spacing is also important when relating the relative degree of porosity in different portions of the covering 30, because two portions may be more or less porous either because the pores in a given region have different average pore diameters, or because the pores are spaced closer or farther apart, or both. The corollary to this is pore density since, if the pores are spaced farther apart in a given region of the covering 30, the pore density in that portion will be less, and vise versa.

While pore diameter is an important parameter for describing the relative size of a pore in different regions of the stent covering 30, and will generally suffice to characterize the desired sizes of most generally regularly shaped pores, e.g., circular, polygonal etc., the shortest pore width is an important factor effecting how the stent covering 30 and pores will interact with the surrounding physiological environment. The surfaces of the covering material 30, whatever their size or shape, provide a guide for cells to grow on, and the pores both create and provide access to these surfaces. However, in regions where either the pore diameter or the shortest pore width is greater than about 150 micrometers, dense cellular ingrowth is less efficient. This is because the distance between the cells or tissue in the center of the void and the material surface is too large, and results in less mature connective tissue penetrating the stent covering 30. Conversely, in regions where either the pore diameter or the shortest pore width is less than about 30 micrometers, the void may be too small to allow cellular ingrowth. Thus, in regions where the stent covering 30 is intended to promote tissue ingrowth and re-endothelialization, the pore diameter preferably ranges from about 30 to about 120 micrometers. In pores or voids having a pore diameter in excess of about 30 micrometers, it is also desirable that the shortest pore width is not less than 30 micrometers and not greater than 120 micrometers. These ranges provide for the most efficient and densest tissue ingrowth and capillary infiltration. The ingrowth of cells and connective tissue into the stent covering's pores will also aid in securing the stent.

It is to be understood that the foregoing dimensions are also desirable inside the pores, in the volume of the stent covering 30, but that for purposes of characterizing the pores of the invention, the dimensions at the surface are most readily measured and quantified by known techniques, such as by optical microscopy, scanning electron microscopy (SEM), water permeability, or bubble pressure techniques. Of course, when the stent covering 30 is made from woven or braided fibers, or by laser drilling, the pore dimensions and shape may be fairly regular, both at the surface and through the volume of the covering 30. In the case of fairly regular pore shapes, pore diameter will generally suffice to characterize the desired pore. By contrast, when pores are formed by dissolving portions of the covering 30 by chemical action, the pore dimensions and shape may tend to vary more significantly. In this case, the shortest pore width becomes a more important dimension since it affects whether tissue will grow into the void forming the pore. The important aspect is that in those areas where healthy tissue ingrowth is desired, the stent covering 30 has a higher degree of porosity and the pore diameters, and preferably also the shortest pore width, are conducive to such growth; and, in those areas where damaged tissue ingrowth is to be deterred, the stent covering 30 has a lower degree of porosity and the pore openings inhibit or prevent such growth.

The pore spacing, or average distance between the pores at the outer surface of the stent covering 30 is also important for establishing how the stent covering will interact with the surrounding physiological environment. Typically, when a phagocytic cell recognizes a surface to be very large in relation to itself, it will not attempt to engulf the foreign material and cause an inflammatory response, but rather will tend to proliferate on the material. Thus, it is desirable that the pore spacing be large enough to prevent phagocytes from triggering an inflammatory response.

Preferably, the pore spacing may range between one-half of the average pore diameter in a given region, up to about four times the average pore diameter in a given portion of the stent covering 30. Still more preferably, the pore spacing is about 3 to about 4 times the average pore diameter in a portion of the stent covering 30 intended to promote tissue ingrowth. Of course, in those portions of the stent covering 30 intended to be non-porous or substantially non-porous, the pore spacing can be infinite. Suitable pore spacing can be obtained, for example, by controlling the size and spacing of the fibers in a fabric type stent covering 30. For example, as shown in FIG. 5, by selecting the fiber diameter to be greater in size than the spaces between the fibers, i.e., the pore diameter, suitable pore spacing on the surface of the stent covering 30 can be achieved.

Different porosities may be obtained by incorporating multiple fiber diameters, alternative fiber shapes (such as trilobal), multiple yarn sizes, or by varying the spacing between the fibers. Likewise, they may be obtained by laser drilling or chemically treating only those portions of the covering desired to be porous. Thus, a less porous region 13 may be characterized as impermeable, nonporous, or solid, because there are no pores, or because any existing pores are so small, and/or few in quantity, that the stent covering 30 is, in effect, solid or impermeable to body fluids under atmospheric pressure, tissue ingrowth and the like in region 13. For example, an extruded stent covering 30 having pores formed by laser drilling, chemical action on the material or the like, may include an impermeable middle region 13 because no pores were formed in that region of the covering (as conceptually shown in FIG. 5e). By contrast, a stent covering 30 formed by woven, knitted or braided fibers may include a less porous middle region 13 that is essentially impermeable to body fluids or tissue ingrowth because of the density or tightness of the weave, knit or braid. In such an embodiment pores may exist at a microscopic level, but the pores are so small or few in number that the middle portion 13 of the stent covering 30 is, in effect, impermeable to significant tissue ingrowth and the like.

FIG. 3 shows an endoprosthesis implant 10 in accordance with the present invention implanted in a blood vessel 16. Preferably, the end portions 12 of the stent covering 30 are more porous than the middle portion 13 of the stent covering 30. As shown in FIG. 4, the more porous end portions 12 promote ingrowth of healthy tissue 14. Because the middle portion 13 is less porous, it inhibits tissue ingrowth.

The use of a nonuniform porosity stent covering 30 provides several advantages. Unlike stent coverings having uniform porosity, the nonuniform porosity stent covering 30 can control tissue healing response and optimize endovascular ingrowth by customizing the placement and amount, e.g. pore size and/or pore density, of porosity on the stent covering 30. Thus, the present invention promotes complete re-endothelialization of long stents and reduces the likelihood of intimal hyperplasia, rendering improved vessel patency. The porosity of the end regions 12 is adapted to permit healthy cells, capillaries, and tissue 14 to penetrate into and/or through the stent covering 30, creating and maintaining a healthy intima 55. As shown in FIG. 4, the diseased segment 15 of the blood vessel 16 is prevented from travelling to the newly formed intimal lining 55 by its encapsulation between the blood vessel wall 56 and the less porous portion 13 of the stent covering 30.

As alluded to above, the stent covering's pores may be filled with a material, such as a drug or protein, to further control the type of tissue penetrating the covering 30. Anti-platelet and anti-thrombotic agents such as heparin, aspirin, or ticlopidine, may be embedded in the pores. Anti-sense, nitric oxide, growth factors, and other agents, may also be embedded in the pores. The agents may be embedded alone or incorporated in another medium, such as collagen, albumin, or gelatin.

Endoprostheses implants may also be used in other, non-cardiovascular passageways and ducts in the body, such as the bronchi, esophagus, and biliary ducts. A nonuniform n porosity stent covering 30 according to the invention can be adapted to be used in any passageway where site specific tissue ingrowth, re-endothelialization or the like is desired. For example, strictures of the biliary duct caused by a tumor may utilize a stent to open the stricture, but the tumor cells can grow through the stent frame and occlude the duct. A nonuniform porosity stent covering 30 may be used in such a case, whereby the middle portion 13, having minimal or no porosity, directly opposes the tumor while the more porous ends 12 of the cover 30 are fixed by healthy tissue ingrowth 14. In this way, the cancer cells 15 cannot easily migrate through the covering 30.

A nonuniform porosity stent covering 30 can be prepared from any suitable biocompatible polymer material known in the art, such as PTFE, polyethylene terephthalate, or silicone, because, as known in the art, they are substantially inert, biocompatible, resilient, and possesses long-term durability and healing performance. Preferred polymers are polycarbonate polyurethane, such as those manufactured by PolyMedica Biomaterials, Inc. under the trademark ChronoFlex or by Thermedics, Inc. under the trademark Carbothane. The polymer can consist of an extruded tube, a continuous polymer sheet connected along opposite edges, or a braided, woven, or knitted fabric, or other fiber matrix. Typically, polymer fabrics consist of multifilament yarns, each yarn being composed of from about 25 to 100 fibers, and each fiber ranging from about 10 to 20 micrometers in diameter. The selection of yarn will naturally dictate the resultant mechanical properties such as percent elongation, fatigue strength, burst strength, and permeability to water. The selection of suitable materials for a given stent application will be apparent to those of ordinary skill in the art in view of the instant disclosure.

The stent covering 30 may be disposed on any suitable stent having an expandable frame structure 22. Most stents have either a self-expanding, balloon expanding, or thermal expanding metallic frame design. A preferred stent is disclosed in U.S. Pat. No. 5,019,090 to Pinchuk. Another suitable is manufactured by Johnson & Johnson Interventional Systems under the trademark Palmaz. Such stents are available in differing sizes. For example, stent lengths may be about 1.5, 3.0, 5.0, 7.0, or 10.0 centimeters. The expanded diameter of a stent may have a range of about 4–7 millimeters diameter or a range of about 8–12 millimeters diameter. In the case of the balloon expandable stent, the stent is manufactured to have an initial diameter smaller than its expanded diameter and a little greater than the uninflated balloon diameter. Stents can be expanded to any diameter in the disclosed ranges. Typically, the stent is expanded to about 10–20% larger than the blood vessel diameter. In the case of balloon expandable stents, the expanded diameter of the stent will generally depend on the diameter and inflation pressure of the balloon.

Any suitable fabrication technique known in the art may be used to achieve the desired porosities and dispose the covering 30 on the stent. If the stent covering 30 is made of a polymer sheet, the stent covering 30 can, for example, have pores laser drilled or dissolved by chemical action and, for example, be heat shrink onto the stent. If the stent covering 30 is made of a fibrous material, then the pores can be formed by weaving, knitting, or braiding the fibers directly onto the stent. A woven material has sets of yarn (either warp or weft) interlaced at right angles; that is, one yarn runs along the length of the stent and the other around the circumference. Weaves typically have strong longitudinal and hoop strength. A knitted material has sets of yarn interlooped around each other. Because of this structure, knits are typically not as strong as weaves and have a tendency to dilate over time. A braided material has sets of yarn interlaced at different angles. A braid typically provides less resistance to longitudinal deformation. Changes in the pitch angle between yarns affects the hoop strength and porosity of the material. The hoop strength of the braid may be increased by constraining the ends of the braid.

Figure 7:
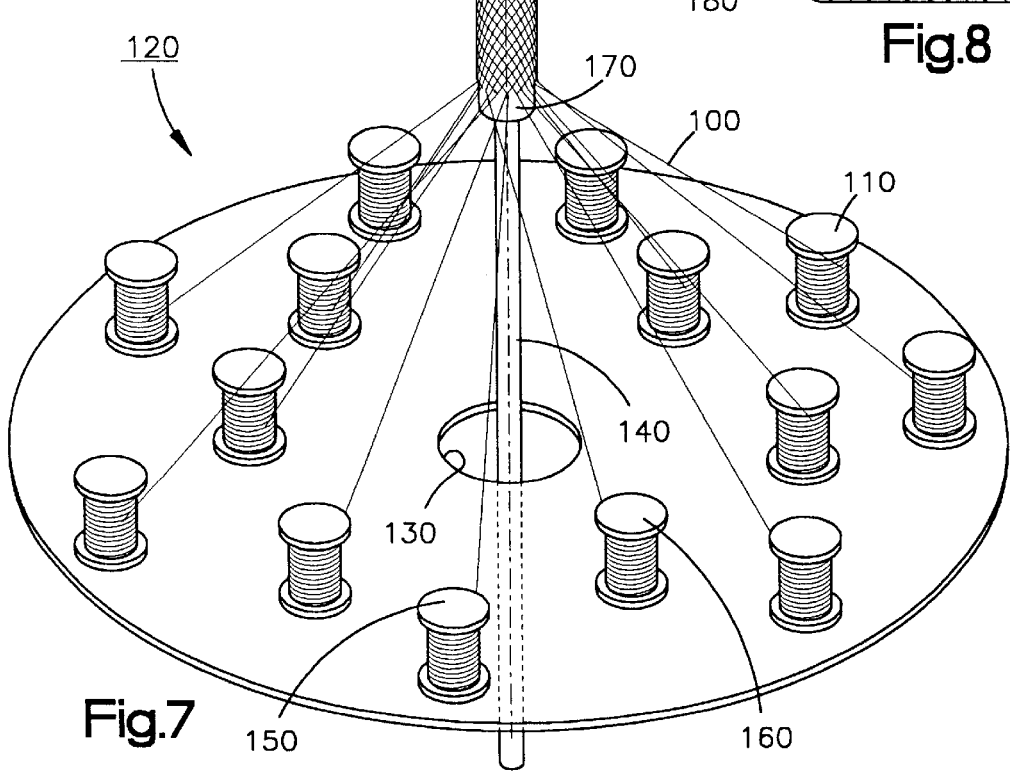
FIG. 7 is a schematic depiction of a braiding machine showing an endoprosthesis implant being braided on a mandrel.

FIG. 7 conceptually shows a braiding machine 120 that may be used to fabricate the covering 30. The cover 30 is braided directly onto the stent 170 as hereinafter described. Any suitable polymer fabric 100 which has been fiber-spun and wound on a bobbin 110 may be selected. Sixteen bobbins 150, 160 are fitted onto sixteen carriers (not shown) on a braiding machine 120. The braiding machine 120 has a hole 130 for a mandrel 140 which the sixteen carriers move around in two opposing directions, eight clockwise 150, and eight counterclockwise 160. The stent 170 is crimped on the mandrel 140 and passed through the center of the sixteen revolving yarn carriers as the carriers rotate at a set speed. The stent 170 moves through the center of the rotating bobbins 150, 160 causing the yarn 100 to braid onto the stent 170 outer diameter. The braiding machine 120 provides several techniques to control the structure and properties of the braid, including the amount of tension in the yarn 100, the pitch of the braid, and the number of overbraids. After the braiding is completed the stent covering 30 may be annealed in an oven at 110° C. to relieve tension in the yarn 100, as well as to fuse overlapping yarns 100 together.

Figure 8:
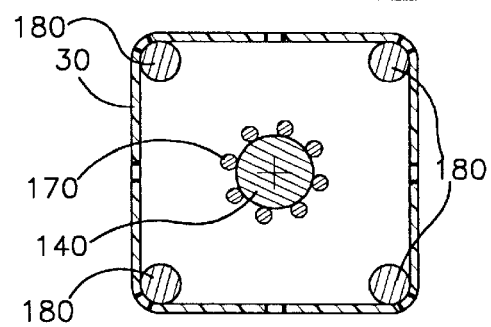
FIG. 8 is a sectional view of a wire fixture for expanding a diameter of the stent covering.

In a preferred embodiment, the braiding is performed directly on the mandrel 140. The mandrel 140 is covered with the desired number of layers of polyurethane yarn 100 to create the stent covering 30. The covering 30 is then annealed in an oven at approximately 80° C. for about five minutes. The covering 30 is slid off of the mandrel 140 and cut to the desired stent 170 length. As shown in FIG. 8, the covering 30 is expanded by a wire fixture 180 to about 0.2 inch diameter. The stent 170 is placed within the inside diameter covering 30. The wire fixture 180 is then removed allowing the covering 30 to contract or recoil onto the stent 170.

While the present invention has been described with a degree of particularity, it is the intent that the invention include all modifications and alterations from the disclosed design falling within the spirit and scope of the appended claims.

What is claimed is:

1. An endoprosthesis implant comprising:
   a) a stent having an expandable frame structure;
   b) a stent covering disposed on said stent, said stent covering having opposed ends, a first region of the stent covering comprising portions of the stent covering adjacent the opposed ends and a second region of the stent covering comprising a middle portion of the stent covering interposed between the first region portions;
   c) the first region having a plurality of pores extending between an inner surface and a spaced apart outer surface of the stent covering defining a first porosity, and the second region having a second porosity different than said first porosity, said second porosity being defined by said second region having fewer pores than said first region; and
   d) each pore in the first region having a pore diameter at the stent covering outer surface of from about 30 to about 120 micrometers.

2. The endoprosthesis implant according to claim 1 wherein an average distance between adjacent pores in the first region being at least about 3 times an average pore diameter of the pores in the first region.

3. The endoprosthesis implant according to claim 1 wherein the stent covering is substantially cylindrical.

4. The endoprosthesis implant according to claim 1 wherein said second region has a plurality of pores each having a pore diameter at the stent covering outer surface that is smaller than 30 micrometers.

5. The endoprosthesis implant according to claim 1 wherein said second region has substantially no pores.

6. The endoprosthesis implant according to claim 1 wherein said second region is substantially impermeable to passage of body fluids under atmospheric pressure.

7. The endoprosthesis implant according to claim 1 wherein said stent covering comprises a plurality of fibers, said fibers having an average diameter that is larger than an average pore diameter of said pores in said first region.

8. The endoprosthesis implant according to claim 7 wherein said fibers have an average diameter of at least about three times said average pore diameter of the pores in the first region.

9. The endoprosthesis implant according to claim 1 wherein said pores in said first region have a shortest pore width of not less than about 30 micrometers and not greater than about 120 micrometers.

10. The endoprosthesis implant according to claim 7 wherein said fibers are woven.

11. The endoprosthesis implant according to claim 7 wherein said fibers are braided.

12. The endoprosthesis implant according to claim 7 wherein said fibers are knitted.

13. The endoprosthesis implant according to claim 1 wherein said stent covering comprises a substantially continuous polymeric sheet having pores interspersed in at least said first region, said pores having an average pore diameter and being spaced apart an average distance that is greater than said average pore diameter.

14. The endoprosthesis implant according to claim 13 wherein said pores are spaced apart an average distance of at least about 3 times said average pore diameter.

15. The endoprosthesis implant according to claim 13 wherein said pores are disposed only in said first region.

16. The endoprosthesis implant according to claim 13 wherein said second region is substantially impermeable to passage of body fluids under atmospheric pressure.

17. The endoprosthesis implant according to claim 13 wherein said pores have a shortest pore width of not less than about 30 micrometers and not greater than about 120 micrometers.

18. The endoprosthesis implant according to claim 1 wherein said pores in said first region have an average pore diameter and are spaced apart an average distance that is greater than said average pore diameter.

19. An endoprosthesis implant comprising:

a) a stent having an expandable frame structure;

b) a stent covering disposed on said stent, said stent covering including a first region having a structure adapted to promote tissue ingrowth, and a second region having a structure adapted to inhibit tissue ingrowth;

c) the first region having a plurality of pores extending between an inner surface and a spaced apart outer surface of the stent covering defining a first porosity and the second region having a second porosity different than the first porosity, each pore in the first region having a pore diameter at the stent covering outer surface of from about 30 to about 120 micrometers; and d) an average distance between adjacent pores in the first region being at least about 3 times an average pore diameter of the pores in the first region.

20. The endoprosthesis implant according to claim 19 wherein said stent covering is substantially cylindrical and has opposed ends, and said first region comprises portions of said stent covering adjacent said opposed ends, and said second region comprises a middle portion of said stent covering interposed between said first region portions.

21. The endoprosthesis implant according to claim 19 wherein said stent covering comprises a substantially continuous polymeric sheet having voids interspersed therein in at least said first region, said voids in said first region having an average diameter and being spaced apart a distance effective to promote tissue ingrowth into said stent covering in said first region, said second region having no voids, or voids having a diameter and spacing effective to inhibit tissue ingrowth h into said stent covering in said second region.

22. The endoprosthesis implant according to claim 21 wherein said average diameter of said voids in said first region is from about 30 to about 120 micrometers, and said voids in said first region are spaced apart an average distance of at least about 3 times said diameter of said voids in said first region.

23. The endoprosthesis implant according to claim 21 wherein said stent covering is substantially cylindrical and has opposed ends, and said first region comprises portions of said stent covering adjacent said opposed ends, and said second region comprises a middle portion of said stent covering interposed between said first region portions.

* * * * *